United States Patent [19]

Erpenbach et al.

[11] Patent Number: 4,898,966
[45] Date of Patent: Feb. 6, 1990

[54] PROCESS FOR THE PREPARATION OF PHENYLALANINE N-PROPYL ESTER HYDROCHLORIDE

[75] Inventors: Heinz Erpenbach, Cologne; Klaus Gehrmann; Peter Hörstermann, both of Erftstadt; Erhard Jägers, Bornheim; Georg Kohl, Hürth, all of Fed. Rep. of Germany

[73] Assignee: Hoechst Aktiengesellschaft, Frankfurt am Main, Fed. Rep. of Germany

[21] Appl. No.: 256,052

[22] Filed: Oct. 11, 1988

[30] Foreign Application Priority Data

Oct. 24, 1987 [DE] Fed. Rep. of Germany ....... 3736078

[51] Int. Cl.⁴ .......................................... C07C 101/10
[52] U.S. Cl. ...................................................... 560/38
[58] Field of Search ........................................... 560/38

[56] References Cited

U.S. PATENT DOCUMENTS 3,941,831  3/1976  Sollman ................................. 560/38
3,983,162  9/1976  Schlatter .............................. 560/38
4,680,403  7/1987  Hisamitsu et al. .................... 560/38

OTHER PUBLICATIONS

"Mass-Transfer Operations", Robert E. Treytbal, McGraw-Hill Book company, Inc., 1955, pp. 344–347.
"Design of Equilibrium Stage Processes", William L. Bolles, McGraw-Hill Book Company, Inc., 1963, pp. 398–399 and 440–441.
Beilsteins Handbuch der Organischen Chemie, 4th Edition, vol. 14, Part 3, Beilstein-Institut, Springer-Verlag Berlin, 1985, pp. 1556–1557.

*Primary Examiner*—Bruce Gray

[57] ABSTRACT

In order to prepare phenylalanine n-propyl ester hydrochloride, phenylalanine hydrochloride is reacted with n-propanol in the molar ration 1: (5 to 20) at temperatures from 80° to 110° C., preferably 85° to 105° C., at pressures from 0.1 to 1.5 bar in the presence of 0.1 to 0.75 mole of HCl/mole of phenylalanine hydrochloride as catalyst and in the presence of water entrainer, a concentration of water entrainer of 20 to 50% by weight being maintained in the reaction mixture.

4 Claims, 1 Drawing Sheet

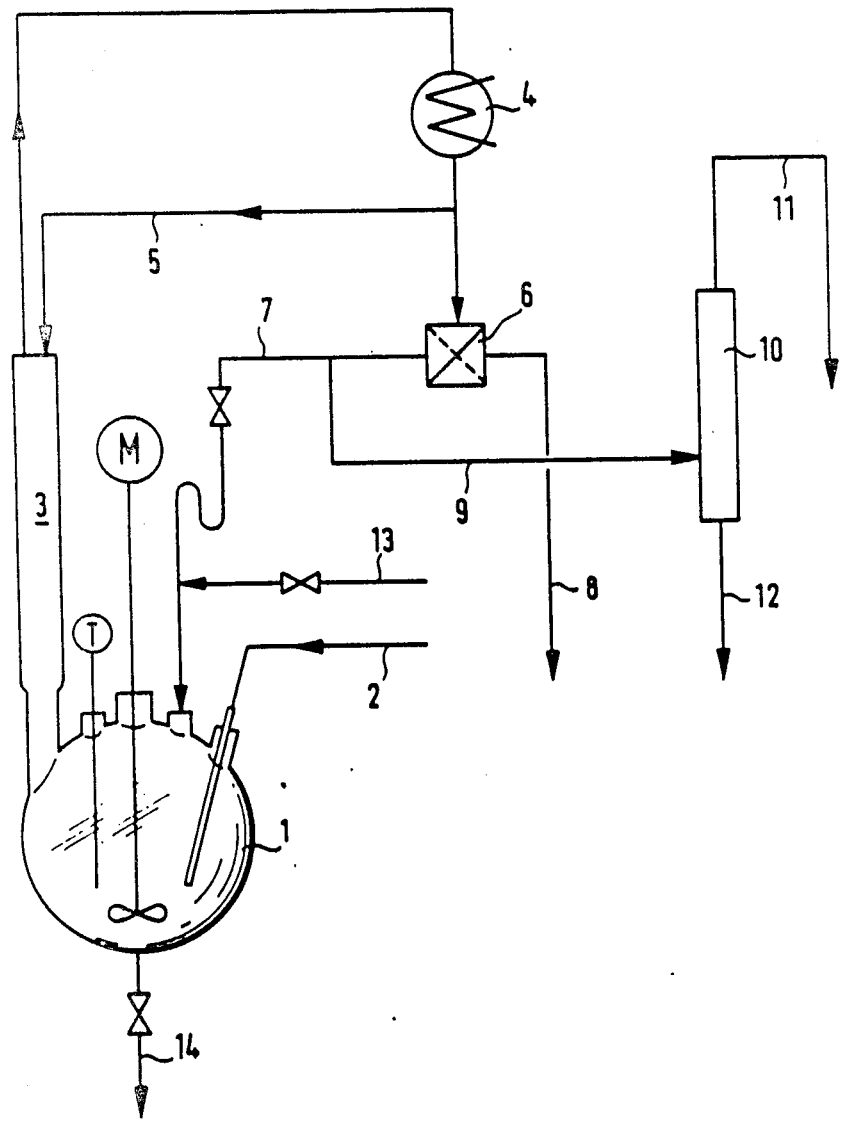

PROCESS FOR THE PREPARATION OF PHENYLALANINE N-PROPYL ESTER HYDROCHLORIDE

The present invention relates to a process for the preparation of phenylalanine n-propyl ester hydrochloride by reacting phenylalanine hydrochloride with n-propanol in the liquid phase in the presence of HCl as catalyst.

It is known to obtain D,L-phenylalanine propyl esters by reacting D,L-phenylalanine with HCl-containing n-propanol in the liquid phase (cf. "Beilsteins Handbuch der Organischen Chemie" [Beilstein's Handbook of Organic Chemistry], 4th edition, 1985, 4th supplement, Volume 14, Part 3, page 1556).

The known reaction is an equilibrium reaction, which means that the degree of conversion into the phenylalanine n-propyl ester is limited by the equilibrium constants. It is therefore necessary to remove, and re-react, unreacted starting materials from the phenylalanine n-propyl ester formed; this state of affairs causes problems in transferring the reaction to an industrial scale and is therefore disadvantageous.

In order to increase the conversion of phenylalanine into phenylalanine n-propyl ester, it is necessary to employ a molar excess of n-propanol of up to 50 fold, relative to the phenylalanine employed, to maintain a high HCl concentration, and to remove the water formed during the reaction by azeotropic distillation together with a large amount of n-propanol. It is advantageous in this process that, on the one hand, the water-containing n-propanol distilled off can only be re-used for reaction after expensive drying and, on the other hand, undesired byproducts, such as di-n-propyl ether and n-propyl chloride, are formed. When sulfuric acid or organic sulfonic acids are used, the catalysts remaining in the esterification residue represent a particular environmental problem which can only be overcome with difficulty.

The object of the present invention is to indicate a process for the preparation of phenylalanine n-propyl ester hydrochloride from phenylalanine hydrochloride and n-propanol which does not have the disadvantages mentioned and in which, instead, the reaction proceeds in good yields with a smaller excess of n-propanol and a reduced amount of HCl as acidic catalyst. This is achieved according to the invention in that phenylalanine hydrochloride is reacted with the n-propanol in the molar ratio 1: (5 to 20) at temperatures from 80° to 110° C., preferably 85° to 105° C., at pressures from 0.1 to 1.5 bar in the presence of 0.1 to 0.75 mole of HCl/mole of phenylalanine hydrochloride and in the presence of a water entrainer, a concentration of water entrainer of 20 to 50% by weight being maintained in the reaction mixture.

In addition, the process according to the invention may optionally have the further features that
(a) the water entrainer used is toluene;
(b) the water entrainer used is 1,2-dichloroethane;
(c) an HCl concentration of 0.15 to 1.5% by weight is produced and maintained in the reaction mixture by metering in 0.1 to 0.75 mole of HCl/mole of phenylalanine hydrochloride;
(d) the entrainer is removed by distillation during the reaction as an azeotrope with water at a reflux rate of 3 to 10, and the organic phase is fed back, at least partly, into the reaction mixture after the phases have been separated;
(e) the entrainer and the excess n-propanol are substantially removed by distillation when the esterification is complete, the bottom product remaining is taken up in additional toluene or xylene, the remaining propanol is removed by distillation, and, after the hot solution has been cooled, the pure crystalline phenylalanine n-propyl ester hydrochloride is obtained therefrom by filtration and subsequent drying.

In the process according to the invention, a satisfactory reaction rate with only low-level formation of n-propyl chloride is achieved by carrying out the esterification reaction at temperatures from 80° to 110° C.; this is because the formation of n-propyl chloride is favored by high temperatures.

In the process according to the invention, the starting material employed can be either phenylalanine hydrochloride directly or phenylalanine itself, the phenylalanine in the reaction mixture being converted into the hydrochloride by additionally introducing hydrogen chloride.

EXAMPLE 1 (COMPARISON EXAMPLE)

5 kg of D,L-phenylalanine hydrochloride (25 mol) and 40 kg of n-propanol (670 mol), which corresponds to a molar ratio of about 1:27, are introduced into a stirred glass reactor 1 (cf. the FIGURE) of capacity 100 l with internal heating coil, which could be heated by an oil circuit controlled by a flow heater. By introducing 850 g of gaseous HCl (23.4 mol) via line 2, an HCl concentration of 0.7% by weight was produced and maintained in the reaction mixture. This corresponds to a D,L-phenylalanine hydrochloride:HCl molar ratio of 1:0.94. The water liberated during the reaction was distilled off, at a reactive temperature of 98° C. and at atmospheric pressure, as an azeotropic mixture, together with n-propanol, which at the same time served as an entrainer, via the head of a column 3 attached to the stirred reactor 1. The azeotrope was removed by condensation in the condenser 4 while setting a constant reflux routed via line 5. The reaction time until complete esterification of the D,L-phenyl-alanine hydrochloride was 6 hours, this only being achievable when, at a reflux rate of 5, 2.6 kg of distillate (containing 4.7% by weight of water, 1% by weight of HCl 7.2% by weight of n-propyl chloride and the remainder of n-propanol) were withdrawn per kg of ester produced. n-Propyl chloride and water can only be removed from this distillate with difficulty and at extremely high cost.

When the esterification of the D,L-phenylalanine hydrochloride was complete, the excess n-propanol was removed by distillation at atmospheric pressure. When a bottom temperature of 102° C. had been reached, the heating was switched off briefly and 25 kg of xylene were added via line 13. The remaining n-propanol was then removed by distillation at 280 mbar, and the hot xylene solution was discharged into the crystallization vessel via line 14. On cooling while stirring, pure D,L-phenylalanine n-propyl ester hydrochloride precipitated out and was filtered off. After drying, 5.9 kg of D,L-phenylalanine n-propyl ester hydrochloride (24.2 mol) were produced in 99% purity, which corresponds to an ester yield of 97.5%. The molar ratio between the n-propyl chloride formed and the D,L-phenylalanine n-propyl ester hydrochloride was 0.6.

EXAMPLE 2 (ACCORDING TO THE INVENTION)

10 kg of D,L-phenylalanine hydrochloride (50 mol), 26.4 kg of n-propanol (440 mol), 19.4 kg of toluene and 0.5 kg of hydrochloric acid (31% strength), which corresponds to a D,L-phenylalanine hydrochloride:n-propanol molar ratio of 1:8.8, were introduced into the stirred reactor 1 used in Example 1 (cf. the FIGURE). During the esterification, 465 g of gaseous HCl (12.75 mol) were introduced via line 2, and an HCl concentration of 0.7% by weight was thus produced and maintained in the reaction mixture. The total amount of HCl added corresponds to a D,L-phenylalanine hydrochloride:HCl molar ratio of 1:0.34. The reaction temperature was 96° C., and the time until complete esterification was 8 hours. Within this period of time, at a reflux rate of 7, 0.96 kg of distillate were withdrawn via the column 3 attached to the reactor 1 per kg of ester produced. The distillate produced in the condenser 4 was separated into two phases in the separator 6; 18% of an aqueous phase and 82% of an organic phase. While the aqueous phase, which comprised about 23% by weight of n-propanol, 1% by weight of toluene, 4.5% by weight of HCl and the remainder of water, was withdrawn via line 8, the organic phase was fed back into the reactor 1 via line 7 until a content of about 14% by weight of n-propyl chloride had been reached. About 70% of the entire organic phase produced, which contained 2.2% by weight of water, 21% by weight of propanol and the remainder of toluene in addition to the stated amount of n-propyl chloride, were subsequently fed to a separation stage 10 via line 9 and separated by distillation at atmospheric pressure at a reflux rate of 6 up to a bottom temperature of 74° C. and a head temperature of 50° C. During this procedure, 0.9 kg of distillate containing 97.5% by weight of n-propyl chloride (11.2 mol) were produced via line 11, while the bottom product, comprising propanol and toluene, withdrawn via line 12 was re-used in the next batch.

When esterification of the D,L-phenylalanine hydrochloride employed was complete, the remaining toluene and the excess n-propanol were removed by distillation via the head of column 3 and, after condensation in the condenser 4, withdrawn via line 8. When a bottom temperature of about 102° C. had been reached, the heating was interrupted and xylene (39 kg) was transferred into the reactor 1 via line 13.

The toluene and the remaining n-propanol were subsequently removed by distillation at a pressure of 280 mbar and a reflux rate of 1. The distillate obtained was used in the next batch without further treatment.

The hot xylene solution was discharged into a crystallization vessel. During cooling with stirring, pure D,L-phenylalanine n-propyl ester hydrochloride crystallized out and was filtered off. After drying, 12 kg of D,L-phenylalanine n-propyl ester hydrochloride (49.5 mol) were obtained in 99.5% purity, which corresponds to an ester yield of 99%. The molar ratio between the n-propyl chloride formed and D,L-phenylalanine n-propyl ester hydrochloride was 0.23.

EXAMPLE 3 (ACCORDING TO THE INVENTION)

10 kg of D,L-phenylalanine hydrochloride (50 mol), 32 kg of n-propanol (530 mol), 20 kg of 1,2-dichloroethane and 0.5 kg of hydrochloric acid (31% strength), which corresponds to a D,L-phenylalanine hydrochloride:n-propanol molar ratio of 1:10.6, were introduced into the stirred reactor 1 used in Example 1 (cf. the FIGURE). During the esterification, 325 g of gaseous HCl (9 mol) were introduced via line 2, and an HCl concentration of 0.7% by weight was thus produced and maintained in the reaction mixture. The total amount of HCl added corresponds to a D,L-phenylalanine hydrochloride:HCl molar ratio of 1:0.27. The reaction temperature was 94° C. and the time until complete esterification was 6.5 hours. Within this period of time at a reflux rate of 5, 1.3 kg of distillate were withdrawn via the column 3 attached to the reactor 1 per kg of ester produced. The distillate produced in the condenser 4 was separated into two phases in the separator 6; 12% of an aqueous phase and 88% of an organic phase. While the aqueous phase, which comprised about 18% by weight of n-propanol, 7% by weight of HCl and the remainder of water, was withdrawn via line 8, the organic phase was fed back into the reactor 1 via line 7 until a content of about 9% by weight of n-propyl chloride had been reached. About 50% of the total organic phase produced, which contained 7% by weight of propanol and the remainder of 1,2-dichloroethane in addition to the stated amount of n-propyl chloride, were subsequently fed to a separation stage 10 via line 9 and separated by distillation at atmospheric pressure at a reflux rate of 6 up to a bottom temperature of 77° C. and a head temperature of 50° C. During this procedure, 0.65 kg of distillate containing 96% by weight of n-propyl chloride (7.9 mol) was produced via line 11, while the bottom product, comprising propanol and 1,2-dichloroethane, withdrawn via line 12 was re-used in the next batch.

When esterification of D,L-phenylalanine hydrochloride was complete, the remaining 1,2-dichloroethane and the excess n-propanol were removed by distillation via the head of column 3 and withdrawn via line 8 after condensation in the condenser 4. When a bottom temperature of about 102° C. had been reached, the heating was interrupted and xylene (39 kg) was introduced into the reactor 1 via line 13. The 1,2-dichloroethane and the remaining n-propanol were subsequently removed by distillation at a pressure of 280 mbar and a reflux rate of 1. The distillate obtained was used in the next batch without further treatment.

The hot xylene solution was discharged into a crystallization vessel. During cooling while stirring, pure D,L-phenylalanine n-propyl ester hydrochloride crystallized out and was filtered off. After drying, 12 kg of D,L-phenylalanine n-propyl ester hydrochloride (49.5 mol) were obtained in 99.5% purity, which corresponds to an ester yield of 99%. The molar ratio between the n-propyl chloride formed and D,L-phenylalanine n-propyl ester hydrochloride was 0.16.

EXAMPLE 4 (ACCORDING TO THE INVENTION)

10 kg of D,L-phenylalanine hydrochloride (50 mol), 28.2 kg of n-propanol (470 mol), 27.8 of toluene and 0.5 kg of hydrochloric acid (31% strength), which corresponds to a D,L-phenylalanine hydrochloride:n-propanol molar ratio of 1:9.4, were introduced into the stirred reactor 1 used in Example 1 (cf. the FIGURE). During the esterification, 480 g of gaseous HCl (13.15 mol) were introduced via line 2, and an HCl concentration of 0.7% by weight was thus produced and maintained in the reaction mixture. The total amount of HCl added corresponds to a D,L-phenylalanine hydrochloride:HCl molar ratio of 1:0.35. The reaction temperature was 96° C. and the time until complete esterification was 7 hours. Within this period of time, at a reflux rate of 7, 0.96 kg of distillate were withdrawn via the column 3 attached to the reactor 1 per kg of ester produced. The distillate produced in the condensor 4 was separated into two phases in the separator 6; 18% of an aqueous phase and 82% of an organic phase. While the aqueous phase, which comprised about 23% by weight of n-propanol, 1% of toluene, 4.5% by weight of HCl and the remainder of water, was withdrawn via line 8, the organic phase was fed back into the reactor 1 via line 7 until a content of about 14% by weight of n-propyl chloride had been reached. About 70% of the total organic phase produced, which contained 2.2% by weight of water, 21% by weight of n-propanol and the remainder of toluene in addition to the stated amount of n-propyl chloride, were subsequently fed to a separation stage 10 via line 9 and separated by distillation at atmospheric pressure at a reflux rate of 6 up to a bottom temperature of 74° C. and a head temperature of 50° C. During this procedure, 0.925 kg of distillate containing 97% by weight of n-propyl chloride (11.6 mol) were produced via line 11, whereas the bottom product, comprising propanol and toluene, withdrawn via line 12 was re-used in the next batch.

When esterification of D,L-phenylalanine hydrochloride employed was complete, toluene and excess n-propanol were removed by distillation via the head of column 3 and withdrawn via line 8 after condensation in the condenser 4. When a bottom temperature of about 102° C. had been reached, the heating was interrupted and additional toluene (35 kg) was introduced into the reactor 1 via line 13. The remaining n-propanol was subsequently removed by azeotropic distillation with toluene at a pressure of 280 mbar and a reflux rate of 1. The distillate obtained was used in the next batch without further treatment.

The hot toluene solution was discharged into a crystallization vessel via line 14. During cooling while stirring, pure D,L-phenylalanine n-propyl ester hydrochloride crystallized out and was filtered off. After drying, 12 kg of D,L-phenylalanine n-propyl ester hydrochloride (49.5 mol) were obtained in 99.4% purity, which corresponds to an ester yield of 99%. The molar ratio between the n-propyl chloride formed and D,L-phenylalanine n-propyl ester hydrochloride was 0.23.

EXAMPLE 5 (ACCORDING TO THE INVENTION)

10 kg of L-phenylalanine hydrochloride (50 mol), 29.4 kg of n-propanol (490 mol), 20.2 kg of toluene and 0.5 kg of hydrochloric acid (31% strength), which corresponds to an L-phenylalanine hydrochloride:n-propanol molar ratio of 1:9.8, were introduced into the stirred reactor 1 used in Example 1 (cf. the FIGURE). During the esterification, 475 g of gaseous HCl (13 mol) were introduced via line 2, and an HCl concentration of 0.7% by weight was thus produced and maintained in the reaction mixture. The total amount of HCl added corresponds to an L-phenylalanine hydrochloride:HCl molar ratio of 1:0.345. The reaction temperature was 96° C. and the time until complete esterification was 7 hours. Within this period of time at a reflux rate of 7, 0.97 kg of distillate were withdrawn via the column 3 attached to the reactor 1 per kg of ester produced. The distillate produced in the condenser 4 was separated into two phases in the separator 6; 18% of an aqueous phase and 82% of an organic phase. While the aqueous phase, which comprised about 23% by weight of n-propanol, 1% by weight of toluene, 4.5% by weight of HCl and the remainder of water, was withdrawn via line 8, the organic phase was fed back into the reactor 1 via line 7 until a content of about 14% by weight of n-propyl chloride had been reached. About 70% of the total organic phase produced, which contained about 2.2% by weight of water, 21% by weight of propanol and the remainder of toluene in addition to the stated amount of n-propyl chloride, were subsequently fed to a separation stage 10 via line 9 and separated by distillation at atmospheric pressure at a reflux rate of 6 up to a bottom temperature of 74° C. and a head temperature of 50° C. During this procedure, 0.92 kg of distillate containing 97.2% by weight of n-propyl chloride (11.4 mol) were produced via line 11, whereas the bottom product, comprising propanol and toluene, withdrawn via line 12 was re-used in the next batch.

When esterification of the L-phenylalanine hydrochloride employed was complete, toluene and the excess n-propanol were removed by distillation via the head of column 3 and withdrawn via line 8 after condensation in the condenser 4. When a bottom temperature of about 102° C. had been reached, the heating was interrupted and xylene (38 kg) was introduced into the reactor 1 via line 13. The toluene and the remaining propanol were subsequently removed by distillation at a pressure of 280 mbar and a reflux rate of 1. The distillate obtained was used in the next batch without further treatment.

The hot xylene solution was discharged into a crystallization vessel. During cooling while stirring, pure L-phenylalanine n-propyl ester hydrochloride crystallized out and was filtered off. After drying, 12 kg of L-phenylalanine n-propyl ester hydrochloride (49.5 mol) were obtained in 99.5% purity, which corresponds to an ester yield of 99%. The molar ratio between the n-propyl chloride formed and the L-phenylalanine n-propyl ester hydrochloride was 0.23.

In the process according to the invention, separation of the n-propyl chloride from the organic phase is entirely without problems, whereas the n-propyl chloride and water can only be separated from the distillate produced in the comparison example with difficulty and at extremely high cost.

The unreacted n-propanol produced overall in the process according to the invention can be used, without a drying step, together with the entrainer for a new esterification batch, whereas the n-propanol from the comparison example is contaminated with water and n-propyl chloride.

The advantages achieved over the comparison example using the examples according to the invention can be seen from the table below.

TABLE

| Example | D,L-phenylalanine hydrochloride:HCl molar ratio | kg of distillate for removal of the water of reaction per kg of ester | | n-propyl chloride: ester molar ratio | phenylalanine n-propyl ester hydrochloride | |
|---|---|---|---|---|---|---|
| | | without reflux | with reflux | | yield [%] | purity [%] |
| 1 comparison | 1:0.94 | 2.6 | 15.6 | 0.60 | 97.5 | 99.0 |
| 2 invention | 1:0.34 | 0.96 | 7.7 | 0.23 | 99.0 | 99.5 |
| 3 invention | 1:0.27 | 1.3 | 7.8 | 0.16 | 99.0 | 99.5 |
| 4 invention | 1:0.35 | 0.96 | 7.7 | 0.23 | 99.0 | 99.4 |
| 5 invention | 1:0.345 | 0.97 | 7.8 | 0.23 | 99.0 | 99.5 |

We claim:

1. A process for the preparation of phenylalanine n-propyl ester hydrochloride, which comprises reacting phenylalanine hydrochloride with n-propanol in a molar ratio 1:(5 to 20) at temperatures from 80° to 110° C. and pressures from 0.1 to 1.5 bar in the presence of 0.1 to 0.75 mole of HCl/mole of phenylalanine hydrochloride and in the presence of an entrainer selected from the group consisting of toluene and 1,2-dichloroethane, a concentration of said entrainer of 20 to 50% by weight being maintained in the reaction mixture, and said entrainer being removed by distillation during the reaction as an azeotrope with water at a reflux rate of 3 to 10, the organic phase being fed back, at least partly, into the reaction mixture after the phases have been separated.

2. The process as claimed in claim 1, wherein an HCl concentration of 0.15 to 1.5% by weight is maintained in the reaction mixture by metering in 0.1 to 0.75 mole of HCl/mole of phenylalanine hydrochloride.

3. The process as claimed in claim 1, wherein the reaction of the phenylalanine hydrochloride is carried out at temperatures from 85° to 105° C.

4. The process as claimed in claim 1, wherein the entrainer and the excess n-propanol are substantially removed by distillation when the esterification is complete, the bottom product remaining is taken up in additional toluene or xylene, the remaining propanol is removed by distillation, and, after the hot solution has been cooled, the pure crystalline phenylalanine n-propyl ester hydrochloride is obtained therefrom by filtration and subsequent drying.

* * * * *